United States Patent [19] [11] 3,948,996
Henrick et al. [45] Apr. 6, 1976

[54] NOVEL PRODUCTS

[75] Inventors: Clive A. Henrick; John B. Siddall, both of Palo Alto, Calif.

[73] Assignee: Zoecon Corporation, Palo Alto, Calif.

[22] Filed: Oct. 9, 1973

[21] Appl. No.: 404,633

Related U.S. Application Data

[60] Division of Ser. No. 256,605, May 24, 1972, Pat. No. 3,826,804, which is a continuation-in-part of Ser. No. 201,189, Nov. 22, 1971, abandoned, which is a continuation-in-part of Ser. No. 191,812, Oct. 22, 1971, abandoned.

[52] U.S. Cl. .............................................. 260/593 R
[51] Int. Cl.² ........................................ C07C 49/20

[58] Field of Search ................................ 260/593 R

[56] References Cited
UNITED STATES PATENTS
3,737,442   6/1973   Baum ................................ 260/399
3,752,843   8/1973   Henrick et al. ................. 260/593 R Primary Examiner—James O. Thomas, Jr.
Assistant Examiner—James H. Reamer
Attorney, Agent, or Firm—Donald W. Erickson

[57] ABSTRACT

Aliphatic di-unsaturated esters and acids, and derivatives thereof, substituted with thiol (mercapto) or hydrocarbon thio group useful for the control of insects.

4 Claims, No Drawings

NOVEL PRODUCTS

This is a division of application Ser. No. 256,605, filed May 24, 1972, now U.S. Pat. No. 3,826,804, which is a continuation-in-part of application Ser. No. 201,189, filed Nov. 22, 1971, now abandoned, which, in turn, is a continuation-in-part of application Ser. No. 191,812, filed Oct. 22, 1971, now abandoned.

This invention relates to novel aliphatic di-unsaturated esters and acids, derivatives thereof, intermediates therefor, substituted with thiol (mercapto) or a hydrocarbon thio group, syntheses thereof, and the control of insects. More particularly, the novel unsaturated esters and acids of the present invention are represented by the following formula A:

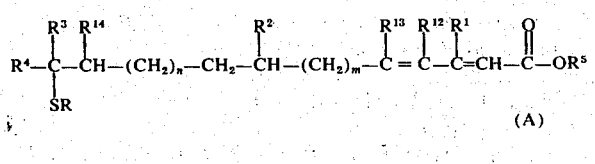

(A)

wherein, each of $m$ and $n$ is zero or the positive integer one, two or three;

R is hydrogen, lower alkyl, cycloalkyl, aralkyl or aryl;

each of $R^1$ and $R^2$ is lower alkyl;

each of $R^3$, $R^{12}$, $R^{13}$ and $R^{14}$ is hydrogen or lower alkyl;

$R^4$ is alkyl; and $R^5$ is hydrogen, lower alkyl, cycloalkyl, aryl, aralkyl, lower alkylthiaalkyl, lower alkoxyalkyl, halogen substituted lower alkyl, heterocyclic, lower alkenyl lower alkynyl or a metal cation, and the acid halides thereof.

The compounds of formula A are useful for the control of insects. The utility of these compounds as insect control agents is believed to be attributable to their juvenile hormone activity. They are preferably applied to the immature insect, namely — during the embryo, larvae or pupae stage in view of their effect on metamorphosis and otherwise cause abnormal development leading to death or inability to reproduce. These compounds are effective control agents for Hemipteran such as Lygacidae, Miridae and Pyrrhocoridae; Lepidopteran such as Pyralidae, Noctuidae and Gelechiidae; Colcepteran such as Tenebrionidae, Crysomelidae and Dermestidae; Dipteran such as mosquitos, flies; Homopteran such as aphids and other insects. The compounds can be applied at low dosage levels of the order of 0.01 μg. to 25.0 μg. per insect. Suitable carrier substances include liquid or solid carriers, such as water, acetone, xylene, mineral or vegetable oils, talc, vermiculite, natural and synthetic resins and silica. Treatment of insects in accordance with the present invention is accomplished by spraying, dusting or exposing the insects to the vapor of the compounds of formula A. Generally, a concentration of less than 25% of the active compound is employed. The formulations can include insect attractants, emulsifying agents or wetting agents to assist in the application and effectiveness of the active ingredient. In the application of the compounds, there is generally employed a mixture of the C-2,3 trans and cis isomers.

In the description hereinafter, each of $m$, $n$, R–$R^5$ and $R^{12}$–$R^{14}$ is as defined hereinabove unless otherwise specified.

The compounds of formula A can be prepared according to the following outlined syntheses:

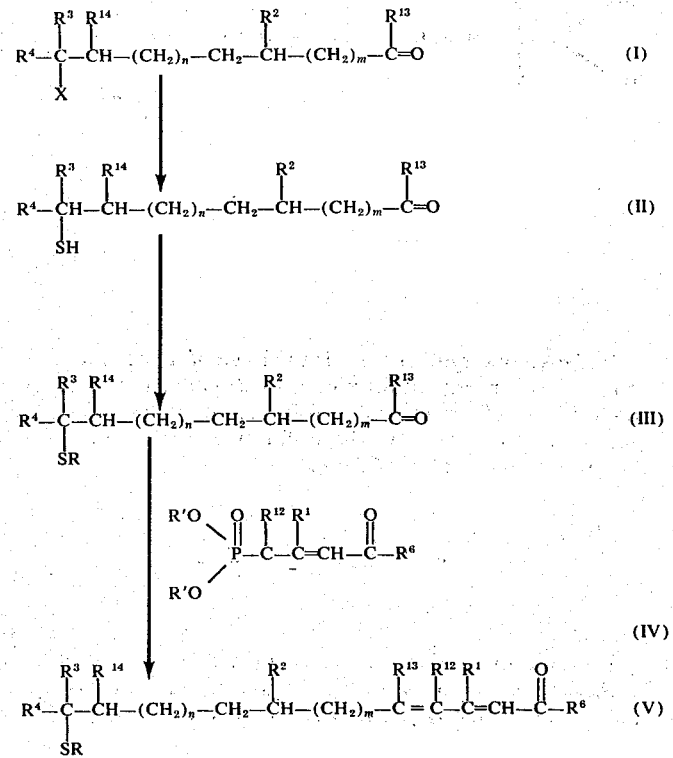

In the above formulas, X is bromo or chloro, R' is lower alkyl, cycloalkyl, benzyl or phenyl and $R^6$ is lower alkoxy, cycloalkoxy or aralkoxy.

In the above synthesis, a ketal or acetal of a carbonyl of formula I is converted into a thiol (mercapto) substituted ketal or acetal of the carbonyl of formula II. Preparation of the thiol can be accomplished for example, using thiourea followed by treatment with base, such as sodium hydroxide or an amine. Suitable methods applicable for preparation of thiols of formula II from a acetal or ketal of a compound of formula I are described by Cossar et al., J. Org. Chem 27, 93 (1962); Backer, Rec. trav. chim. 54, 215 (1935); Szmuszkovicz, Organic Preparations and Procedures 1 (1), 43–45 (1969); and Backer and Dijkstra Rec. trav. chim. 51, 290 (1932). A compound of formula II, or the acetal or ketal thereof, is then alkylated to prepare a thioether of formula III (R is not H). The alkylation can be accomplished using a halide of the hydrocarbon group desired such as lower alkyl iodide. The acetal or ketal protecting group is removed in a conventional manner using dilute acid such as aqueous hydrochloric acid, aqueous sulfuric acid, and the like. A carbonyl of formula III is then reacted with a carbanion of formula IV to prepare the dienoic ester of formula V (R is not hydrogen). Reaction of the carbanion with a carbonyl of formula II provides the mercapto compounds of formula V (R is hydrogen). The carbanion is generated from the respective phosphonate with a base such as alkali hydroxide, alkali alkoxide, alkali hydride, and the like. Suitable procedures are described by Pattenden and Weedon, J. Chem. Soc. (C), 1984 and 1997 (1968), Corey et al., Tetrahedron Letters No. 2,1821 (1971) and U.S. Pat. Nos. 3,163,669 and 3,177,226.

A second synthesis of esters of formula V is outlined as follows:

Conversion of VI into V using carbanion (IVC) can be done using the same conditions as for conversion of III into V. Wittig reactions are generally done at higher temperatures such as from room temperature to reflux. The ylids are prepared from the corresponding phosphonium bromide or chloride by treatment with a base substance such as alkali metal hydride, alkali metal hydroxide or alkali metal carbonate in an organic solvent, such as toluene, benzene, or tetrahydrofuran, or water or aqueous organic solvent depending upon the particular base. The Wittig reagents can be prepared as described in U.S. Pat. No. 3,193,565.

The esters of formula V are converted into the corresponding acid by hydrolysis with base such as potassium carbonate, sodium carbonate, sodium hydroxide, and the like in organic solvent such as methanol or ethanol. Other esters of the present invention can be prepared by transesterification or conversion of the acid into the acid halide by treatment with thionyl chloride, oxalyl chloride, phosphorous pentabromide or the like, and then reacting the acid halide with the alcohol corresponding to the ester moiety desired.

In another embodiment of the present invention, there is provided thio-acids and thiol esters of formula VII. Thio-acids and thiol esters can be prepared from the respective acid halide using hydrogen sulfide to prepare the thio-acid and a thiol $R^{15}$-SH or a mercaptide to prepare the thiol ester. Thiol esters can be prepared by alkylation of the sodium salt of thio-acid of the present invention also. See U.S. Pat. Nos. 3,567,747 and 3,505,366.

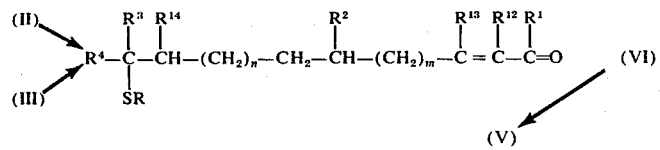

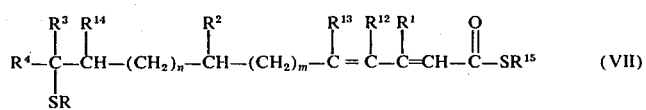

In the second synthesis outlined above of II and III to VI to V, a carbonyl of formula II or III is reacted with a carbanion of formula IV A using the conditions described above or with an ylid of formula IV B to yield an unsaturated ketone of formula VI.

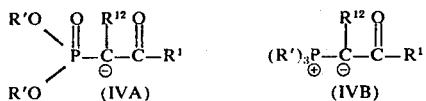

The unsaturated ketone (VI) is then reacted with a carbanion of formula IVC to yield a compound of formula V or by Wittig reaction using the ylid (IVD).

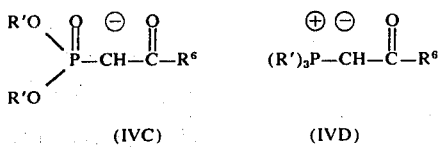

wherein $R^{15}$ is hydrogen, lower alkyl, cycloalkyl, aryl or aralkyl.

In another embodiment of the present invention, there is provided ketones and aldehydes of formula VIII. The ketones can be prepared by treatment of an ester (V) or an acid thereof with the appropriate organo-lithium, the organo group corresponding to the ketone moiety desired. The reaction is generally carried out in an organic solvent such as an ether solvent. In addition, acid halides, particularly the acid chloride, can be used for the preparation of ketones of formula VIII by reaction with lithium diorganocopper, e.g. lithium dimethylcopper, using the procedure of Posner and Whitten, Tetrahedron Letters, No. 53, 4647 (1970).

The aldehydes of formula VIII ($R^{15}$ is hydrogen) can be prepared by the controlled oxidation of an allylic alcohol of formula IX ($R^{16}$ is hydrogen) using chromic acid, manganese dioxide, and the like. The oxidation can be carried out using procedures described by Burrell et al., J. Chem. Soc. (C), 2,144 (1966); Weedon et al., J. Chem Soc. 2687 (1951) and Helv. Chim. Acta 32

1356 (1949). The allylic alcohols of formula IX are prepared by reduction of the corresponding ester or acid of formula A using lithium aluminum hydride or the like.

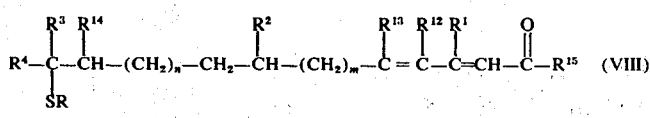

(VIII)

The allylic alcohols of formula IX, i.e. wherein $R^{16}$ is hydrogen, are prepared by reduction of an ester or an acid of formula A. Ethers of formula IX, i.e. wherein $R^{16}$ is not hydrogen, are prepared by etherification of an allylic alcohol of formula IX using conventional etherification methods such as by first converting the allylic alcohol into the corresponding halide of formula X in which X is bromo, chloro or iodo and then reacting the halide with the salt, e.g. the sodium or potassium salt, of an alcohol according to ether moiety desired. The allylic halides serve as precursors for the preparation of the novel thiols and thioethers of formula XI. Thus, reaction of a halide of formula X with, for example, thiourea or hydrogen sulfide provides the novel thiols. The thioethers can be prepared from the allylic halides by reaction with a mercaptide or by etherification of the thiol.

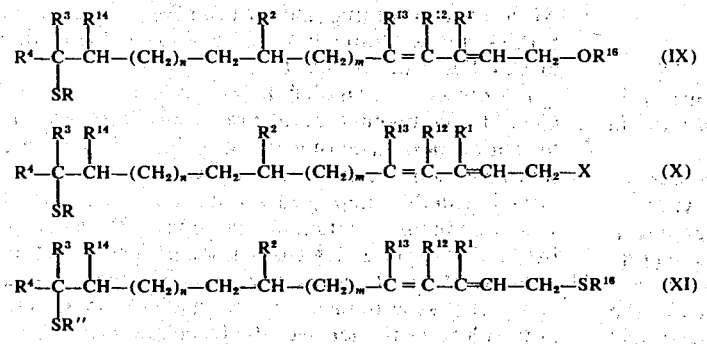

In the above formulas $R^{16}$ is hydrogen, lower alkyl, cycloalkyl, aryl, aralkyl or carboxylic acyl. In formula IX, when R is hydrogen, then $R^{16}$ is hydrogen. In formula XI, R'' is lower alkyl, cycloalkyl, aralkyl or aryl.

In another embodiment of the present invention, there is provided novel amines of formula XII which are prepared by reaction of an allylic halide of formula X with an amine according to the amino moiety desired.

wherein,
each of $R^8$ and $R^9$ is hydrogen, alkyl, alkenyl, cycloalkyl, hydroxyalkyl, alkoxyalkyl, aryl or aralkyl, or when taken together with the nitrogen atom to which they are attached, pyrrolidino, morpholino, piperazino or 4-alkylpiperazino.

In another embodiment of the present invention, there is provided nitriles of formula XIII which can be prepared by reaction of a carbonyl of formula VI with a phosphonacetonitrile of the formula:

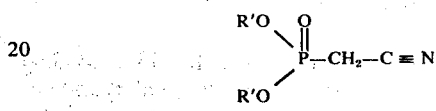

in the presence of base such as an alkali metal hydride or alkali metal alkoxide in an organic solvent such as tetrahydrofuran, benzene, dimethylsulfoxide, toluene, dimethylformamide, ether, and the like. The nitriles of the present invention can be prepared also by treatment of a primary amide of the present invention with sodium borohydride using the procedure of Ellzey. Jr. et al., U.S. Pat. No. 3,493,576. The nitriles of formula XIII can be used as precursors for preparation of the amines of the present invention as by treatment with lithium aluminum hydride, and the like to the respective primary amine.

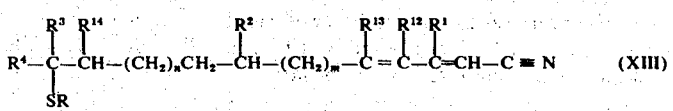

(XIII)

In another embodiment of the present invention, there is provided novel amides of formula XIV

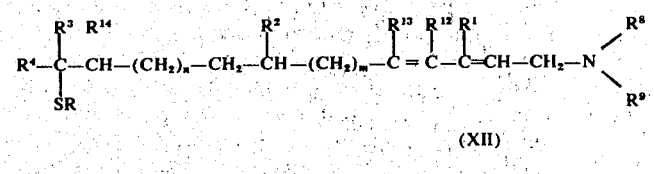

(XII)

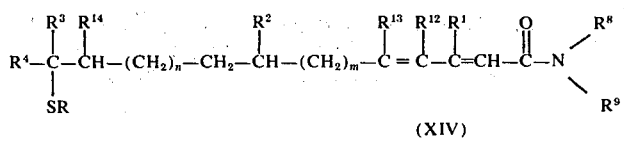

(XIV)

which can be prepared by reaction of an acid chloride or acid bromide of formula A with an appropriate amine selected according to the amido moiety desired. The novel amides of the present invention can be prepared also by the reaction of a carbonyl of formula III with a carbanion of the formula

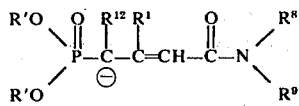

which is generated by treatment of the corresponding phosphonamide with base such alkali metal hydride or alkali metal alkoxide. The amides can be prepared also by reaction of a carbonyl of formula VI with a carbanion or ylid of the following formulas, respectively;

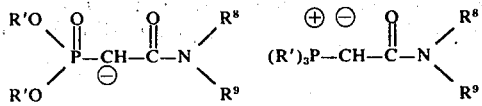

The novel compounds of formulas VII, VIII, IX, XI, XII, XIII and XIV are useful for the control of insects in the same manner as the parent compounds of formula A.

The thioethers described herein are useful precursors for preparing the respective sulfinyl and sulfonyl derivatives by treatment of the thioether with sodium metaperiodate, hydrogen peroxide, or the like, at a temperature of from about 0° to 20°C for about 1 hour or less to about 6 hours to prepare sulfinyl derivatives. The reaction usually affords some of the sulfonyl compound also which can be separated by chromatography or the like, if desired. By using more than one mole of oxidizer per mole of thioether, higher temperature and/or longer reaction time, the formation of the sulfonyl compounds is favored. The sulfinyl and sulfonyl derivatives are useful for the control of insects in the same manner as the thioethers of formula A.

The compounds of formula I and the acetals and ketals of can be prepared from a compound of formula I', the preparation of which is described in application Ser. No. 187,897, filed Oct. 8, 1971, the disclosure of which is incorporated by reference.

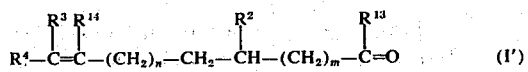

Reaction of an aldehyde of formula I' with hydrogen chloride, acetyl chloride or hydrogen bromide in a lower monohydric alcohol solvent medium provides acetals of formula I. Ketals of formula I can be prepared by ketalization of a ketone of formula I using a lower alkylene glycol such as ethyleneglycol in the presence of an acid catalyst followed by chlorination of bromination. Suitable procedures applicable to the preparation of halides of formula I and acetals and ketals thereof are described in U.S. Pat. Nos. 2,902,510, 3,381,039, 3,428,694 and 3,584,010.

The term "lower alkyl" refers to an alkyl group having a chain length of one to six carbon atoms.

In addition to the compounds of the present invention having activity useful for the control of insects, the compounds have numerous other useful applications. For example, the esters of formula A of the present invention are useful lubricants and plasticizers for polymers such as SRB, polybutadiene, ethylene-propylene copolymers and polypropylene and aid in the processing and application of polymers. The aldehydes and ketones of formulas II, III, VI and VIII are useful in perfumery compositions in view of their odor-imparting properties. Thiolesters of formula VII possess excellent lubricating properties per se and are useful also as lubricant additives. The amides of formula XIV are useful as anti-static agents for synthetic and natural fibers. The amides can be incorporated into the fiber material by blending prior to extrusion or by application to the fiber after extrusion. The amines of formula XII are useful wetting and cleansing agents per se for textiles and as intermediates therefor using the method of U.S. Pat. No. 2,169,976.

The presence of an olefinic bond at position C-2 and C-4 of the compounds of the present invention give rise to four isomers, each of which is embraced by the present invention. As mentioned above, a mixture of isomers is suitably employed for the control of insects such as mixture containing the trans (2), trans (4) isomer and the cis (2), trans (4) isomer. The conditions of the syntheses described herein and the reactants can be selected so as to favor formation of one isomer such as the all trans isomer over the formation of other isomers. The selection of appropriate conditions and reactants to favor formation of one isomer over another will be apparent to those of ordinary skill in the art giving due consideration to the specific examples hereinafter. See also Pattenden and Weedon, supra and Corey et al., supra. In the specific examples hereinafter, when isomerism is not specified, it is understood to include a mixture of isomers which, if desired, can be separated using known separation methods. Hereinafter, when only one designation of configuration is given, the designation refers to position C-2,3 and the configuration is taken to be trans at position C-4,5 when not otherwise specified.

The following examples are provided to illustrate the practice of the present invention. Temperature is given in degrees Centigrade.

EXAMPLE 1

Into a mixture of 10 g. of 3,7-dimethyloct-6-en-1-al and 100 ml. of dry methanol is introduced 1.1 equivalent of dry hydrogen chloride cooling in ice-water. The mixture is then allowed to stand for about 24 hours at room temperature with stirring. Solvent is evaporated and residue taken up in ether which is washed with water, dried and evaporated under reduced pressure to give 1,1-dimethoxy-7-chloro-3,7-dimethyloctane.

The aldehydes under col. I are hydrochlorinated to give the respective compound under col. II.

I 3,7-dimethylnon-6-en-1-al
3-methyl-7-ethylnon-6-en-1-al
3-ethyl-7-methylnon-6-en-1-al
3,6,7-trimethyloct-6-en-1-al
3,6-dimethylhept-5-en-1-al
3,5,6-trimethylhept-5-en-1-al
2,5-dimethylhex-4-en-1-al
2,4,5-trimethylhex-4-en-1-al

II 1,1-dimethoxy-7-chloro-3,7-dimethylnonane
1,1-dimethoxy-7-chloro-3-methyl-7-ethylnonane
1,1-dimethoxy-7-chloro-3-ethyl-7-methylnonane
1,1-dimethoxy-7-chloro-3,6,7-trimethyloctane
1,1-dimethoxy-6-chloro-3,6-dimethylheptane
1,1-dimethoxy-6-chloro-3,5,6-trimethylheptane
1,1-dimethoxy-5-chloro-2,5-dimethylhexane
1,1-dimethoxy-5-chloro-2,4,5-trimethylhexane As an alternative method of preparation, there can be used the following procedure.

To 1.1 equivalents of acetyl chloride and 100 ml. of methanol, at about 10°, is added 10 g. of 3,7-dimethyloct-6-en-1-al. The reaction is allowed to stand for 24 hours at 5°–10° and then allowed to rise to room temperature. After one hour, solvent is removed by evaporation and the concentrate taken up in ether, washed with water and brine, dried over magnesium sulfate and evaporated to yield 1,1-dimethoxy-7-chloro-3,7-dimethyloctane.

EXAMPLE 2

A mixture of 10 g. of 1,1-dimethoxy-7-chloro-3,7-dimethyloctane, one equivalent of thiourea and 100 ml. of 95% ethanol is refluxed for about 24 hours. Then a solution of 1.5 equivalents of sodium hydroxide in 50 ml. of water is added and the mixture refluxed for about 2 hours. After cooling to about room temperature, the solution is carefully acidified and ether is added. The organic layer is separated, washed with water, dried over calcium sulfate and evaporated to give 1,1-dimethoxy-7-mercapto-3,7-dimethyloctane which is purified by distillation.

EXAMPLE 3

To a mixture of 100 ml. of triethylene glycol and 42 g. of thiourea, at 75°–80°, slowly added one equivalent of 1,1-dimethoxy-7-chloro-3,7-dimethyloctane, with stirring, keeping the temperature below 130°. When the reaction mixture is homogeneous, the reaction is continued 12 hours and then one equivalent of tetraethylenepentamine is added slowly. Then the reaction mixture is heated to reflux until the head temperature is constant. The mixture is then distilled to give crude 1,1-dimethoxy-7-mercapto-3,7-dimethyloctane which is purified by fractional distillation.

EXAMPLE 4

A solution of 10 g. of 1,1-dimethoxy-7-chloro-3,7-dimethyloctane, 1.1 equivalents of sodium hydrosulfide and 100 ml. of methanol is refluxed for 24 hours. After cooling, solvent is evaporated under reduced pressure and the concentrate taken up in ether. The ether solution is washed with water, dried over magnesium sulfate and then evaporated to give 1,1-dimethoxy-7-mercapto-3,7-dimethyloctane.

EXAMPLE 5

To 5 g. of magnesium covered with dry ether is added a crystal of iodine and then about 10 ml. of a solution of one equivalent of 1,1-dimethoxy-7-chloro-3,7-dimethyloctane in 200 ml. of ether is added. The mixture is stirred until reaction begins and then remainder of solution is added slowly while heating to reflux. After addition is complete, reflux is continued for 1 hour. After cooling to 25°–30°, solid sulfur (one equivalent) is added portionwise while keeping the temperature about 30°–35°. After addition of the sulfur is complete, the mixture is stirred for about 1 hour and then cooled to 0°–5° and about 200 ml. of aqueous ammonium chloride added slowly while maintaining low temperature. The organic phase is then separated and extracted with 2N sodium hydroxide. The basic extract is cooled in ice, acidified carefully by addition of cold aqueous HCl and extracted with ether. The ether extract is washed with saturated sodium chloride, dried over magnesium sulfate and evaporated to yield 1,1-dimethoxy-7-mercapto-3,7-dimethyloctane which is purified by distillation.

By use of the above procedure or, alternatively the procedure of Example 2, 3 or 4, each of the hydrochlorides under col. II is converted into the respective mercaptan under col. III.

III 1,1-dimethoxy-7-mercapto-3,7-dimethylnonane
1,1-dimethoxy-7-mercapto-3-methyl-7-ethylnonane
1,1-dimethoxy-7-mercapto-3-ethyl-7-methylnonane
1,1-dimethoxy-7-mercapto-3,6,7-trimethyloctane
1,1-dimethoxy-6-mercapto-3,6-dimethylheptane
1,1-dimethoxy-6-mercapto-3,5,6-trimethylheptane
1,1-dimethoxy-5-mercapto-2,5-dimethylhexane
1,1-dimethoxy-5-mercapto-2,4,5-trimethylhexane

EXAMPLE 6

To a mixture of 10 g. of 1,1-dimethoxy-7-mercapto-3,7-dimethyloctane, one equiv. of sodium methoxide and 100 ml. of methanol is added 1.5 equivalents of methyl iodide. The mixture is stirred for 2 hours at room temperature and then refluxed for 2 hours. After cooling to room temperature, solvent is removed by evaporation and the residue taken up in ether. The ether solution is washed with water, dried and evaporated under reduced pressure to give 1,1-dimethoxy-7-methylthio-3,7-dimethyloctane which can be purified by chromatography or distillation.

A mixture of 5 g. of 1,1-dimethoxy-7-methylthio-3,7-dimethyloctane, 50 ml. of aqueous tetrahydrofuran (1:1) and 10 ml. of 3N hydrochloric acid is stirred at room temperature until hydrolysis is completed as followed by thin layer chromatography to give crude 7-metylthio-3,7-dimethyloctan-1-al which is worked up by extraction with ether and purified by chromatography.

Following the procedure of this example, there is prepared the methylthio compounds under col. IV from the respective mercaptan under col. III.

IV 7-methylthio-3,7-dimethylnonan-1-al
7-methylthio-3-methyl-7-ethylnonan-1-al
7-methylthio-3-ethyl-7-methylnonan-1-al 7-methylthio-3,6,7-trimethyloctan-1-al
6-methylthio-3,6-dimethylheptan-1-al
6-methylthio-3,5,6-trimethylheptan-1-al
5-methylthio-2,5-dimethylhexan-1-al
5-methylthio-2,4,5-dimethylhexan-1-al

EXAMPLE 7

Sodium methoxide (1.2 g. of sodium and 30 ml. of methanol) is added slowly to a mixture of 6.4 g. of 7-methylthio-3,7-dimethyloctan-1-al and 10 g. of diethyl 3-methoxycarbonyl-2-methylprop-2-enyl phosphonate (about 77% trans) in 50 ml. of dimethylformamide, under nitrogen and at about 0°, with stirring. After addition is complete, the reaction is left 3 hours at room temperature and worked up by extraction with hexane/ether to yield cis/trans methyl 11-methylthio-3,7,11-trimethyldodeca-2,4-dienoate mostly the trans, trans isomer.

By repeating the above process, using each of the aldehydes under col. IV as the starting material, there is prepared the respective methyl ester under col. V.

V methyl 11-methylthio-3,7,11-trimethyltrideca-2,4-dienoate
methyl 11-methylthio-3,7-dimethyl-11-ethyltrideca-2,4-dienoate
methyl 11-methylthio-3,11-dimethyl-7-ethyltrideca-2,4-dienoate
methyl 11-methylthio-3,7,10,11-tetramethyldodeca-2,4-dienoate
methyl 10-methylthio-3,7,10-trimethylundeca-2,4-dienoate
methyl 10-methylthio-3,7,9,10-tetramethylundeca-2,4-dienoate
methyl 9-methylthio-3,6,9-trimethyldeca-2,4-dienoate
methyl 9-methylthio-3,6,8,9-tetramethyldeca-2,4-dienoate

EXAMPLE 8

To 350 ml. of ethanol, 105 ml. of water and 70 ml. of 50% aqueous sodium hydroxide is added 46.5 g. of methyl 11-methylthio-3,7,11-trimethyldodeca-2,4-dienoate. The mixture is refluxed for about 18 hours. After cooling, alcohol is removed in vacuo. Water is added followed by acidification and then extraction with ether to yield 11-methylthio-3,7,11-trimethyldodeca-2,4-dienoic acid.

By use of the above process, the other esters under col. V are hydrolyzed to the respective free acid.

EXAMPLE 9

To 0.6 g. of 11-methylthio-3,7,11-trimethyldodeca-2,4-dienoic acid in 10 ml. of dry benzene is added 0.23 ml. of oxalyl chloride at room temperature with stirring. After 2 hours, isopropanol (2ml.) is added and the mixture allowed to stand at room temperature for about 2 hours. Ether and saturated sodium bicarbonate is added and the organic phase separated. The organic phase is washed with aqueous sodium bicarbonate, saturated sodium chloride, dried over calcium sulfate and evaporated to yield isopropyl 11-methylthio-3,7,11-trimethyldodeca-2,4-dienoate.

EXAMPLE 10

To 0.6 g. of 11-methylthio-3,7,11-trimethyldodeca-2,4-dienoic acid in 10 ml. of dry benzene is added 0.23 ml. of oxalyl chloride at room temperature. After about 2 hours, there is added 0.25 ml. of 3-thiabutan-1-ol and the reaction allowed to stand for about 2 hours. The reaction is worked up as in Example 9 to yield 3'-thiabutanyl 11-methylthio-3,7,11-trimethyldodeca-2,4-dienoate.

EXAMPLE 11

Sodium ethoxide (9 g. sodium in 600 ml. of ethanol) is added slowly to a mixture of 54.5 g. of 7-methylthio-3,7-dimethyloctan-1-al and 75 g. of diethyl 3-ethoxycarbonyl-2-methylprop-2-enyl phosphonate (about 49% trans) in one liter of dimethylformamide, under nitrogen and at 0°, with stirring. The mixture is allowed to stand overnight at about 5° and the reaction worked up by extraction with ether, washing with water and brine and filtering through Florisil to yield ethyl 11-methylthio-3,7,11-trimethyldodeca-2,4-dienoate as a cis/trans mixture, mostly trans, trans.

EXAMPLE 12

To a solution of 0.5 g. of 11-methylthio-3,7,11-trimethyldodeca-2,4-dienoic acid in 15 ml. of benzene is added, with stirring, an equivalent amount of potassium hydride. The mixture is stirred at room temperature for about 2 hours and then evaporated to give potsssium 11-methylthio-3,7,11-trimethyldodeca-2,4-dienoate.

In place of KH, there can be used KOH, NaOH, and the like to form the corresponding salt.

EXAMPLE 13

To a solution of 2 g. of methyl 11-methylthio-3,7,11-trimethyldodeca-2,4,10-trienoate and 20 ml. of dry ether, at −78° is added slowly about 0.4 g. of lithium aluminum hydride in dry ether. The mixture is allowed to stand about 1 hour after addition is complete and then allowed to warm up to room temperature. Then 2.5 ml. of acetic acid is added. The mixture is then washed with ice water and the organic phase separated which is dried over magnesium sulfate and evaporated to yield 11-methylthio-3,7,11-trimethyldodeca-2,4-dien-1-ol.

EXAMPLE 14

A mixture of 0.18 g. of NaH (rinsed with hexane), 5 ml. of tetrahydrofuran and 0.8 g. of diethyl diethylaminocarbonylmethyl phosphonate, under nitrogen, is stirred 0.5 hours at 0°. To the mixture is slowly added 1.0 g. of 10-methylthio-6,10-dimethylundec-3-en-2-one. After addition is complete, the reaction is left at room temperature for about 30 minutes and then chromatographed on silica with ether to yield N,N-diethyl 11-methylthio-3,7,11-trimethyldodeca-2,4-dienamide (mostly trans-2-trans-4), which can be further purified by chromatography.

EXAMPLE 15

To sodium hydride (0.7 g.), previously washed with hexane, under nitrogen, is added 75 ml. of dry tetrahydrofuran and then, after cooling to 0°, 5.1 g. of diethyl phosphonoacetonitrile is added slowly. The mixture is stirred for about 30 minutes and then added slowly to 6.8 g. of 10-methylthio-6,10-dimethylundec-3-en-2-one at room temperature with stirring. The mixture is stirred for about 12 hours and then poured into saturated sodium chloride at 0°. The layers are separated and the organic layer dried over magnesium sulfate and evaporated to yield 11-methylthio-3,7,11-trimethyldodeca-2,4-dienenitrile.

EXAMPLE 16

To a stirred solution of 2.5 g. of 11-methylthio-3,7,11-trimethyldodeca-2,4-dienoic acid in 20 ml. of dry ether is added slowly at 0°, 23 ml. of a one molar solution of ethyl lithium in benzene. After about 3 hours at 20°, the mixture is poured into iced 1N hydrochloric acid (100 ml.) with vigorous stirring. The ether layer is separated, combined with ethereal washings of the aqueous phase, washed with water, saturated potassium bicarbonate and then saturated brine, dried over magnesium sulfate and concentrated under reduced pressure to yield 13-methylthio-5,9,13-trimethyltetradeca-4,6-dien-3-one, which can be purified by chromatography.

By using methyl lithium, cyclopentyl lithium and phenyl lithium in the above process in place of ethyl lithium, there is prepared 12-methylthio-4,8,12-trimethyltrideca-3,5-dien-2-one, cyclopentyl 10-methylthio-2,6,10-trimethylundeca-1,3-dienyl ketone and phenyl 10-methylthio-2,6,10-trimethylundeca-1,3-dienyl ketone, respectively.

EXAMPLE 17

Sodium ethoxide (prepared from 0.2 g. of sodium and 12 ml. of ethanol) is slowly added to a mixture of 1.1 g. of 7-methylthio-3,7-dimethyloctan-1-al, diethyl 3-ethoxycarbonyl-2-methyl-prop-2-enyl-phosphonate (1.6 g.) and 50 ml. of dimethylformamide, with stirring, under nitrogen, at 0°. The reaction is stirred for 1.5 hours after addition is complete and then worked up by extraction with ether to yield ethyl 11-methylthio-3,7,11-trimethyldodeca-2,4-dienoate.

EXAMPLE 18

To a mixture of 10 g. of 7-methylthio-3,7-dimethyloctan-1-al, 17 g. of diethyl 3-ethoxycarbonyl-2-methylprop-2-enyl-phosphonate (77% trans), and 150 ml. of dimethylformamide, under nitrogen, 0°, with stirring, is added sodium isopropanolate (prepared from 1.5 g. of sodium in 150 ml. of isopropanol). After addition is complete, the reaction is stirred for 18 hours at room temperature and then worked up by extraction with hexane to yield isopropyl 11-methylthio-3,7,11-trimethyldodeca-2,4-dienoate (mostly trans-2,trans-4) which can be chromatographed and distilled for further purification.

EXAMPLE 19

A mixture of 5 g. of 7-mercapto-3,7-dimethyloctan-1-al 8.5 g. of di-isopropyl 3-ethoxycarbonyl-2-methylprop-2-enyl-phosphonate, and 40 ml. of dimethylformamide, under nitrogen and cooled in an ice-bath, is stirred for 0.5 hours and then ground NaOH (1.165g.) is added. The reaction mixture is stirred at room temperature for 3 hours and then hexane-water (1/1) added. The organic layer is washed with water and brine, dried over calcium sulfate and concentrated. The concentrate is filitered through Florisil using hexane and hexane/ether. The filtrate is concentrated and then distilled to yield ethyl 11-mercapto-3,7,11-trimethyldodeca-2,4 -dienoate (mostly trans-2, trans-4).

The process of this example is repeated with the exception of using di-isopropyl 3-isopropoxy carbonyl-2-methylprop-2-enyl-phosphonate to prepare isopropyl 11-mercapto-3,7,11-trimethyldodeca2,4-dienoate.

EXAMPLE 20

To a mixture of 20 ml. of benzene, one ml. of ethylene glycol and 10 mg. of p-toluenesulfonic acid is added 500 mg of 7-chloro-3,7-dimethyloctan-1-al. The mixture is refluxed for 16 hours and water is removed by means of a Dean-Stark trap. After cooling to room temperature, the mixture is poured into ether and washed with aqueous sodium bicarbonate and then water. After drying over calcium sulfate, solvent is reomved under reduced pressure to yield the ethylene ketal (1,1-cycloethylenedioxy-7-chloro-3,7-dimethyloctane).

The procedure of this example can be used to prepare the other cycloethylene ketals of the carbonyls of formula I.

EXAMPLE 21

A mixture of 4 g. of citronellol (3,7-dimethyloct-6-en-1-ol), 0.490 g. of p-toluenesulfonic acid and 0.290 g. of hydroquinone is placed in a stainles steel screw cap bomb having an internal volume of 45 ml. The bomb is cooled in dry ice. Methyl mercaptan (9 g.) is introduced directly into the bomb through the valve head. The bomb is sealed, left overnight at room temperature and then heated to 220° in an oil bath for about 72 hours. After cooling in dry ice, the bomb valve is opened and the reaction mixture is carefully poured into 5% aqueous sodium hydroxide solution. Ether is added and the organic layer is separated, washed with 5% NaOH, 5% HCl and water, dired over calcium sulfate and concentrated with vacuo to yield 7-methylthio-3,7-dimethyloctan-1-ol.

EXAMPLE 22

Twenty grams of citronellol, 2 g. of p-toluenesulfonic acid and 9 g. of methyl mercaptan are reacted as described in Example 44 except that a temperature of 140° is used instead of 220°, to give 7-methylthio-3,7-dimethyloctan-1-ol.

EXAMPLE 23

To 2.04 g. (10 mmol.) of 7-methylthio-3,7-dimethyloctan-1-ol in 25 ml. of freshly distilled dimethylsulfoxide, under nitrogen at 20°, is added via syringe 11.2 ml. (80 mmol.) of triethylamine while stirring vigorously. Sulfur trioxide-2 pyridine complex (10.28 g., 64 mmol.) in dimethylsulfoxide (50 ml.) is added slowly to the mixture via dropping funnel under the same conditions. After addition is complete, the reaction mixture is stirred for 5 minutes and poured into cold water. Hexane is added and the organic layer separated, washed well with water and dried over calcium sulfate. Evaporation of the solvent at reduced pressure affords 7-methylthio-3,7-dimethyloctan-1-al.

EXAMPLE 24

Sodium ethoxide (490 mg.) is added, during about 10 minutes and under nitrogen, to a stirred solution of diethyl 3-ethoxycarbonyl-2-methylprop-2-enylphosphonate (1.93 g.) and 7-methylthio-3,7-dimethyloctan-1-al (1.35 g.) in 20 ml. of dimethylformamide, cooled to 0°. The reaction mixture is stirred at room temperature for about 16 hours and then is diluted with water and extracted with ether. The ethereal extracts are washed with brine, dried over calcium sulfate and evaporated to yield ethyl 7-methylthio-3,7,11-trimethyldodeca-2,4-dienoate, predominantly the trans, trans isomer, which can be purified by chromatography or distillation.

What is claimed is:

1. A compound selected from those of the following formula:

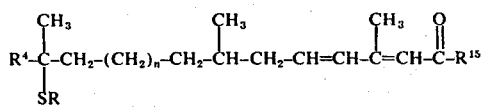

wherein,
$n$ is zero or one;
each of R and $R^4$ is methyl or ethyl; and
$R^{15}$ is lower alkyl.

2. A compound according to claim 1 wherein $R^{15}$ is methyl or ethyl.

3. A compound according to claim 1 wherein $R^{15}$ is ethyl; $n$ is one; and each of R and $R^4$ is methyl.

4. A compound according to claim 1 wherein $R^{15}$ is methyl; $n$ is one; and each of R and $R^4$ is methyl.

* * * * *